(12) United States Patent
Caiafa et al.

(10) Patent No.: US 11,525,768 B2
(45) Date of Patent: *Dec. 13, 2022

(54) ELECTRIC PULSE GENERATION SYSTEM USING CAPACITIVE COUPLING

(71) Applicant: General Electric Company, Schenectady, NY (US)

(72) Inventors: Antonio Caiafa, Albany, NY (US); Vasile Bogdan Neculaes, Niskayuna, NY (US); Allen Lawrence Garner, West Layfayette, IN (US); Andrew Soliz Torres, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 677 days.

This patent is subject to a terminal disclaimer.

(21) Appl. No.: 16/538,616

(22) Filed: Aug. 12, 2019

(65) Prior Publication Data

US 2019/0359970 A1 Nov. 28, 2019

Related U.S. Application Data

(60) Division of application No. 15/955,377, filed on Apr. 17, 2018, now Pat. No. 10,421,956, which is a
(Continued)

(51) Int. Cl.

| | | |
|---|---|---|
| *B01L 3/00* | (2006.01) | |
| *G01N 21/03* | (2006.01) | |
| *C12M 1/42* | (2006.01) | |
| *C12N 13/00* | (2006.01) | |
| *A61B 5/15* | (2006.01) | |
| *H03K 3/53* | (2006.01) | |

(Continued)

(52) U.S. Cl.
CPC ......... *G01N 21/03* (2013.01); *A61B 5/15003* (2013.01); *A61B 5/153* (2013.01); *A61B 5/150343* (2013.01); *A61B 5/150755* (2013.01); *B01L 3/52* (2013.01); *C12M 35/02* (2013.01); *C12N 13/00* (2013.01); *H03K 3/53* (2013.01); *G01N 33/49* (2013.01)

(58) Field of Classification Search
CPC ................................. B01L 3/52; B01L 3/50
USPC .............. 356/246; 422/50, 547, 561, 560
See application file for complete search history.

(56) References Cited

U.S. PATENT DOCUMENTS

| | | | |
|---|---|---|---|
| 5,186,800 A | 2/1993 | Dower | |
| 5,720,921 A * | 2/1998 | Meserol | A61M 1/3696 |
| | | | 435/173.6 |

(Continued)

OTHER PUBLICATIONS

Freitag, Julian et al.; "Photoactivated platelet-rich plasma therapy for a traumatic knee chondral lesion", BMJ Case Reports 2012: doi 10.1136/bcr-2012-006858 (abstract only).

(Continued)

*Primary Examiner* — Christine T Mui
(74) *Attorney, Agent, or Firm* — Fletcher Yoder, P.C.

(57) ABSTRACT

In accordance with the present disclosure, exposure of a sample to one or more electric pulses via capacitive coupling is described. In certain embodiments, the sample may be a biological sample to be treated or modified using the pulsed electric fields. In certain embodiments, the electric pulses may be delivered to a load using capacitive coupling. In other embodiments, the electric pulses may be bipolar pulses.

12 Claims, 6 Drawing Sheets

Related U.S. Application Data continuation-in-part of application No. 15/651,900, filed on Jul. 17, 2017, now Pat. No. 10,329,551, which is a continuation of application No. 14/158,106, filed on Jan. 17, 2014, now Pat. No. 9,708,597.

(51) Int. Cl.
*A61B 5/153* (2006.01)
*G01N 33/49* (2006.01)

(56) References Cited

U.S. PATENT DOCUMENTS

| | | | |
|---|---|---|---|
| 6,010,613 | A | 1/2000 | Walters et al. |
| 6,326,177 | B1 | 12/2001 | Schoenbach et al. |
| 7,053,063 | B2 | 5/2006 | Rubinsky et al. |
| 7,565,201 | B2 | 7/2009 | Blackmore et al. |
| 7,750,605 | B2 | 7/2010 | Ragsdale |
| 7,923,238 | B2 | 4/2011 | Ragsdale |
| 8,173,416 | B2 | 5/2012 | Muller-Hartmann et al. |
| 8,222,909 | B2 | 7/2012 | Ragsdale |
| 9,011,929 | B2 | 4/2015 | Park et al. |
| 9,078,862 | B2 | 7/2015 | Neculaes et al. |
| 9,238,808 | B2 | 1/2016 | Caiafa et al. |
| 2003/0050591 | A1* | 3/2003 | Patrick McHale .. A61K 9/5068 604/4.01 |
| 2009/0023131 | A1 | 1/2009 | Mueller-Hartmann et al. |
| 2009/0212788 | A1 | 8/2009 | Patterson |
| 2011/0259091 | A1 | 10/2011 | Laubscher et al. |
| 2011/0281362 | A1 | 11/2011 | Olson |
| 2014/0106430 | A1 | 4/2014 | Hargrave et al. |
| 2014/0363412 | A1* | 12/2014 | Neculaes ............... A61K 41/00 435/283.1 |

OTHER PUBLICATIONS

AdiStem PhotoActivated PRP & Stem Cell Technology website downloaded 2014: http://www.adistem.com/technology/prp/.

Khine, Michelle, et al.; "Single-cell electroporation arrays with real-time monitoring and feedback control," Lab Chip 2007, 7, 457-462.

JP Application No. 2016-545972; Office Action dated Dec. 20, 2018; 8 pages, including translation.

RU Application No. 2016126427; Office Action, dated Oct. 26, 2018; 6 pages.

TW Application No. 104100402; Office Action, 7 pages.

Xiao, S., et al.; "Pulsed Power for Wound Healing", Frank Reidy Research Center for Bioelectrics, Old Dominion University, 2008, pp. 1-4.

Zhang, Jue, et al.; "Nanosecond Pulse Electric Field (nanopulse): A Novel Non-Ligand Agonist for Platelet Activation", Archives of Biochemistry and Biophysics 471 (2008), pp. 240-248.

* cited by examiner

ELECTRIC PULSE GENERATION SYSTEM USING CAPACITIVE COUPLING

CROSS-REFERENCE TO RELATED APPLICATIONS

This application is a divisional of U.S. patent application Ser. No. 15/955,377, entitled "ELECTRIC PULSE GENERATION SYSTEMS USING CAPACITIVE COUPLING," filed Apr. 17, 2018, which is a continuation-in-part of U.S. patent application Ser. No. 15/651,900, entitled "ELECTRIC PULSE GENERATION SYSTEMS USING CAPACITIVE COUPLING," filed on Jul. 17, 2017, which is a Continuation of U.S. application Ser. No. 14/158,106, entitled "ELECTRIC PULSE GENERATION SYSTEMS USING CAPACITIVE COUPLING," filed on Jan. 17, 2014, each of which is incorporated by reference herein in their entirety for all purposes.

BACKGROUND

The subject matter disclosed herein relates to electric pulse generations systems for biomedical applications and, more specifically, to methods and systems that may employ capacitive coupling to alter shapes in the electric pulsing.

Pulsed power has numerous industrial applications, such as medical treatments, biotechnology, food processing, water treatment (e.g., water purification), exhaust gas treatment, ozone generation, and ion implantation. For example, transfection is a medical technique used to permeabilize cell membranes to facilitate DNA plasmid entry into the cell. This technique, also known as electroporation, typically involves applying electric pulses with sufficient strength and duration to permeabilize the cell membrane while maintaining viability of the cell. Once the cell membrane is rendered "leaky," DNA (e.g., DNA, DNA plasmid, DNA single strands, DNA fragments, etc.) in a surrounding buffer solution passes into the cell. Certain in vivo and ex vivo platelet activation methods also utilize pulsed electrical stimulation.

Oftentimes in medical techniques employing pulsed power, the pulse generation system is directly coupled to the container (e.g., a cuvette) that holds the sample being stimulated. In a directly (i.e., conductively) coupled system, the current associated with the electric pulse flows directly through the sample. Typically, square wave pulses are utilized for electroporation, where one could adjust the pulse width, the pulse amplitude, number of pulses and the frequency. This may be facilitated by using special containers made of a conductive material (i.e., metal), which may be expensive or which may not be suitable for biological or biochemical specimens.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, an electric pulse generation system includes memory, a display, and a user input device. The pulse generation system also includes a sample holder which includes a first and second electrode disposed on either side of a container containing a sample. The pulse generation system includes pulse generating circuitry configured to supply a pulse to the first and second electrodes, and a capacitive element disposed between the pulse generating circuitry and the second electrode. The pulse generating circuitry is capacitively coupled to the container. The pulse generation system also includes a processor configured to execute instructions stored on the memory to control the pulse generating circuitry.

In a second embodiment, an electric pulse generation system includes a memory, a display, and a user input device. The pulse generation system also includes a sample holder that includes a first and second electrode disposed on either side of a container containing a sample. The pulse generation system includes pulse generating circuitry configured to supply a pulse to the first and second electrodes, and a capacitive element disposed between the pulse generating circuitry and the second electrode. The capacitive element may be removable or may be bypassed during operation of the electric pulse generation system. The pulse generation system also includes a processor configured to execute instructions stored on the memory to control the pulse generating circuitry and whether the pulse generating circuitry is directly or capacitively coupled to the sample.

In a third embodiment, a method includes collecting blood from a patient. A configuration of a sequence of one or more electric pulses is specified based on a desired parameter associated with growth factor release. The blood sample or a platelet rich plasma sample derived from the blood sample is then exposed to the sequence of one or more pulsed electric fields via a capacitively coupled pulse generation system to trigger release of a growth factor in the blood sample or the platelet rich plasma.

In a fourth embodiment, an electric pulse generation system may include a memory, a display, and a user input device. The electric pulse generation system may also comprise a sample holder including a first electrode and a second electrode disposed on opposite sides of the sample holder, wherein the sample holder is configured to receive a sample container and pulse generating circuitry configured to supply a first pulse and a second pulse to the first and second electrodes. The first pulse has a pulse duration and a first electric field strength and the second pulse has the pulse duration and a second electric field strength. The first electric field strength and the second electric field strength are additive inverses. The electric pulse generation system may further include a processor configured to execute instruction stored on the memory to control the pulse generating circuitry.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present subject matter will be described below. In an effort to provide a concise description of these embodiments, not all features of an actual implementation may be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Present embodiments relate to a pulse generation system for applications employing pulsed power. Specifically, the embodiments described herein relate to a pulse generation system wherein biological samples are placed in a cuvette or other suitable vessel or container. The pulse generation system may be coupled to the corresponding load by capacitive coupling, and in some embodiments, by both capacitive and direct coupling. If the load may be coupled to the pulse generation system by both capacitive and direct coupling, an operator may select which type of coupling to use. Although the embodiments described herein relate to a specific application, it should be appreciated that these are merely examples of possible uses of the subject matter. Accordingly, the disclosed techniques may be implemented, for example, in other medical treatment applications, biotechnology, food processing, water treatment (e.g., water purification), exhaust gas treatment, ozone generation, and ion implantation. In particular, the samples exposed to the electric pulses may be samples used in medical treatment, biotechnology, food processing, water treatment (e.g., water purification), exhaust gas treatment, ozone generation, and/or ion implantation techniques.

Figure 1:
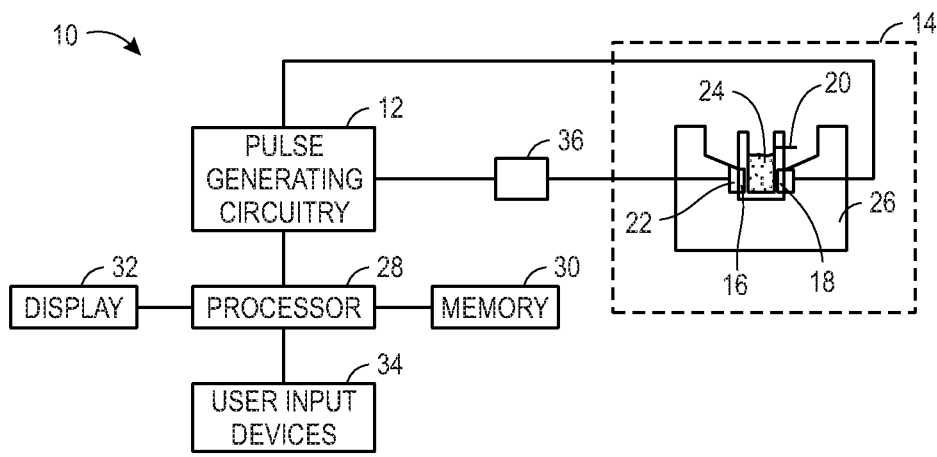
FIG. 1 is a schematic of a capacitively coupled pulse generation system and load, in accordance with an embodiment of the present approach.

With the foregoing in mind, FIG. 1 illustrates a pulse generation system 10. The pulse generation system 10 may include pulse generating circuitry 12 and a load 14. The load 14 may include electrode sets (or array of electrodes) 16 and 18; the electrodes 16 and 18 may be designed to conduct high amounts of current, such as in the range of 0.01 kA-35 kA. In the depicted embodiment, the electrodes 16 and 18 are spaced apart on opposite sides of a cuvette 20. That is, the cuvette 20 is disposed between and contacted by the electrodes 16 and 18 and the electrodes are coupled to the pulse generator via contacts 22. In one embodiment, the cuvette 20 is configured to hold a biological or biochemical sample 24, such as a blood sample. In certain embodiments, the cuvette 20 is disposable and/or is removable from a sample holder 26. Accordingly, insertion of the cuvette 20 and contact of the electrodes 16 and 18 with the contacts 22 allows the pulse generator to produce an electric pulse, and the sample 24 within the cuvette 20 is exposed to the pulses. Although the illustrated embodiment depicts a cuvette 20, it should be appreciated that a cuvette is but one example of a sample container, and that any suitable container configured to hold a sample may be disposed between the electrodes 16 and 18. In certain embodiments, the cuvette 20 or the corresponding sample holder may conduct the electric pulses. The cuvette 20 separates the electrodes 16 and 18 from one another. Though the preceding description describes the cuvette holding a biological sample, it should be appreciated that the load 14 may include any suitable sample that benefits from exposure to electric pulses and the corresponding sample holder.

In certain embodiments, the system 10 may include suitable control and input circuitry and may be implemented in a dedicated housing or may be coupled to a computer or other processor-based system. The system 10 may include a processor 28 that controls the pulse generating circuitry 12. Additional components of the system 10 may include a memory 30 storing instructions executed by the processor 28. Such instructions may include protocols and/or parameters for the electric pulses generated by the pulse generating circuitry 12. The processor 28 may include, for example, general-purpose single-or multi-chip microprocessors. In addition, the processor 28 may be any conventional special purpose processor, such as an application-specific processor or circuitry. The memory 30 may be a mass storage device, a FLASH memory device, removable memory, etc. In addition, a display 32 may provide indications to an operator related to the operation of the system 10. The system 10 may include a user input device 34 (e.g., a keyboard, mouse, touchscreen, trackball, hand held device or controller or any combination thereof) for activating the pulse generating circuitry 12 and/or selecting appropriate parameters.

In the depicted embodiment, the system 10 is used for ex vivo platelet activation. For example, the sample may be a blood product that has been removed from the body and processed to enrich the platelet concentration (e.g., platelet rich plasma). In other embodiments, the system 10 may be used for in vivo techniques. Accordingly, the system 10 may be implemented as a wand or other handheld device with spaced electrodes that delivers an electric pulse in or on a load.

It is envisioned that the pulse generation system 10 as provided herein may be implemented as a single-purpose device (e.g., solely for platelet activation) or as a multi-purpose device that may be used for other electric field exposure applications, such as electroporation, in addition to platelet activation, as discussed herein. Further, the system 10 may be configured to generate an electric pulse according to one or more protocols. The protocols may be based on user inputs of configurable values or parameters and/or may be stored in the memory 30 as pre-set protocols to be selected by the user. In one embodiment, the system 10 may operate without any user input to the activation protocol other than an input to start activation once the sample 24 is loaded. In such an embodiment, the pulse generating circuitry 12 may operate under control of the processor 28 to operate a single protocol with predetermined electric field strength, pulse length, and/or total exposure time. Such a protocol may be determined by empirical or theoretical studies. In other embodiments, the system 10 may be configured to receive a user input related to the electric field strength, pulse length, and/or total exposure time. Further, the system 10 may be configured to generate a particular pulse shape or to generate a series of pulses that may differ from one another according to a user input and/or a stored protocol setting.

The pulses generated by the system 10 may have a duration from about 1 nanosecond to about 100 microseconds, and an electric field strength from about 0.1 kV/cm to 350 kV/cm, depending on the application. The spacing between the electrodes 16 and 18 may influence the strength of the electric field, which is defined as the ratio of the applied voltage and the electrode gap distance. For example, if a cuvette provides a 1 cm gap between the electrodes, exposing the cuvette to 1 kV yields an electric field strength of 1 kV/cm. While the pulses generated by the system may be at least 10 kV/cm, 50 kV/cm, etc., they should not exceed the breakdown field of the sample 24.

In conventional systems, a pulse generation system would be directly coupled to the corresponding load, such that current would flow directly from the pulse generating circuitry to and through the sample. As such, the cuvette, or, generically, the sample container, may be made from a conductive (i.e., metal) material, which may be expensive or otherwise undesirable, such as due to the nature of the sample. Further, the sample may become contaminated due to contact with metallic surfaces. The cuvette 20 may also need to have certain characteristics that reduce the chance of electrical breakdown (e.g., arcing).

To reduce or eliminate the complexity of the sample holder 26, and in the depicted embodiment, the cuvette 20, the pulse generation system 10 may be capacitively coupled to the load 14. The system 10 may include a capacitive element 36 disposed between the pulse generating circuitry 12 and the sample 24, as illustrated in FIG. 1. In some embodiments, the capacitive element 36 may be disposed between the pulse generating circuitry 12, and the electrode 16. In the capacitively coupled system 10, the capacitive element 36 prevents direct current (DC) from flowing through the sample 24, and forces bipolar impulsive currents through the sample.

Figure 2:
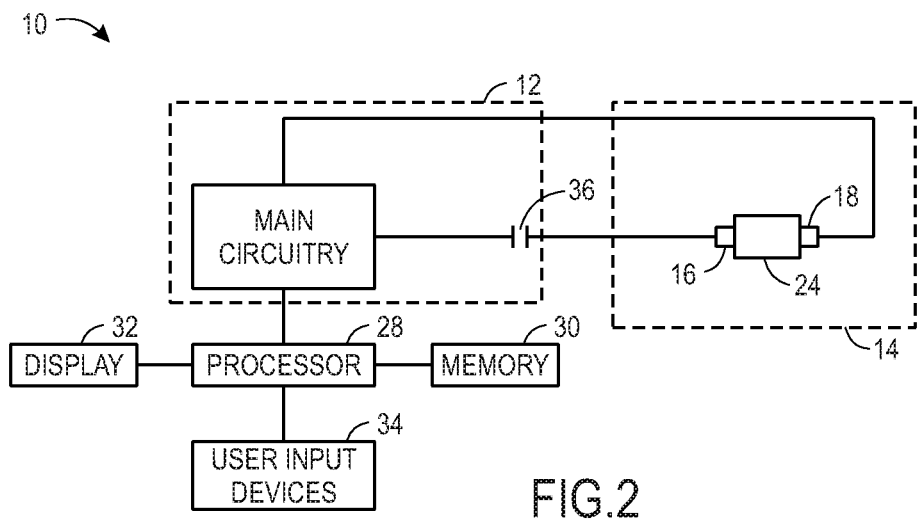
FIG. 2 is a schematic of the pulse generation system and load of FIG. 1, in accordance with an embodiment of the present approach.
Figure 3:
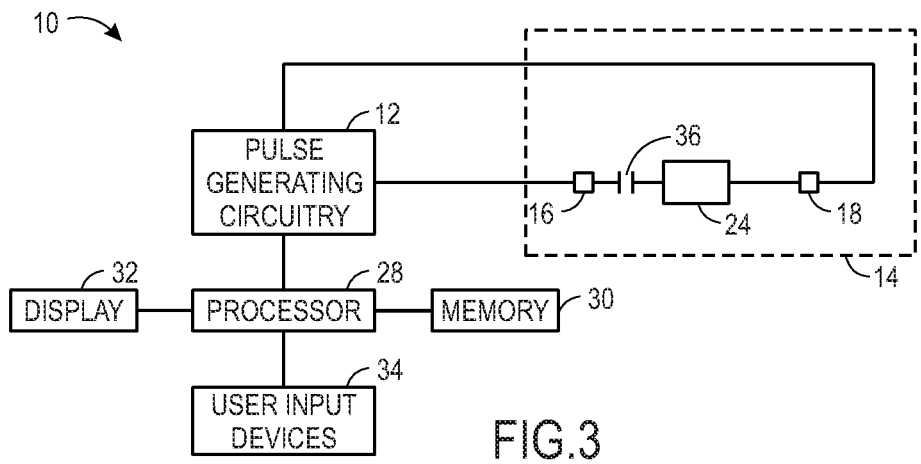
FIG. 3 is a schematic of the pulse generation system and load of FIG. 1, in accordance with another embodiment of the present approach.

The capacitive element 36 may be any suitable component or material that acts as a capacitor and is disposed in series with the sample 24. For example, the capacitive element 36 may be a capacitor disposed at the end of the pulse generating circuitry 12, as illustrated in FIG. 2. A capacitor 36 may also be disposed between the electrode 16 and the sample 24, as illustrated in FIG. 3. For example, a capacitor 36 may be attached to a compartment located between the electrode 16 and the sample holder 26 in a cuvette.

Figure 9:
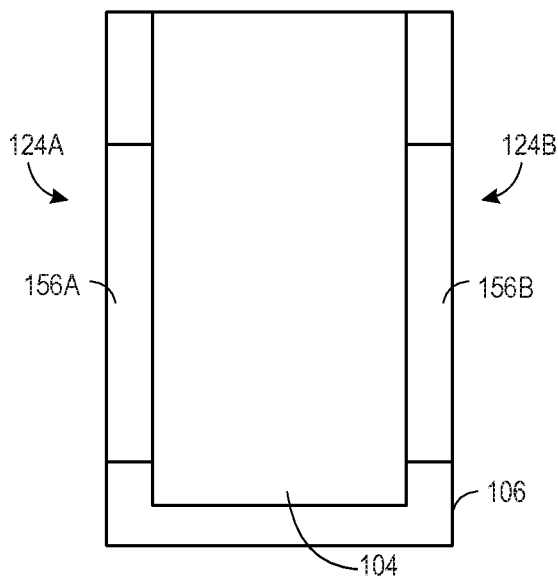
FIG. 9 is a schematic diagram of a traditional cuvette with two conductive terminals.
Figure 10A:
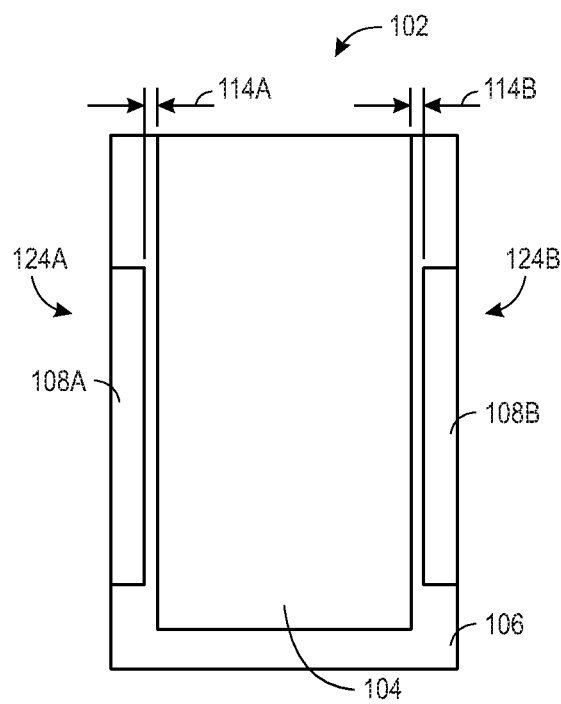
FIG. 10A is a schematic diagram of a cuvette with two conductive terminals, which may include a capacitive element, in accordance with an embodiment of the present approach.
Figure 10B:
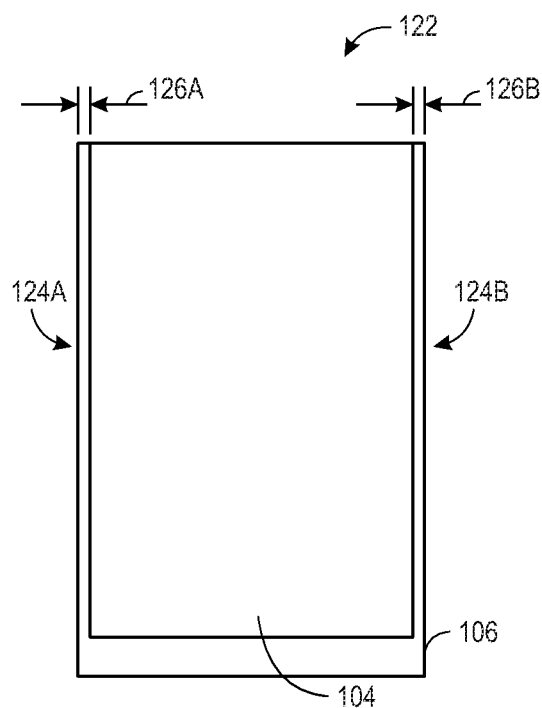
FIG. 10B is a schematic diagram of a cuvette with no conductive terminals, which may include a capacitive element, in accordance with an embodiment of the present approach.
Figure 10C:
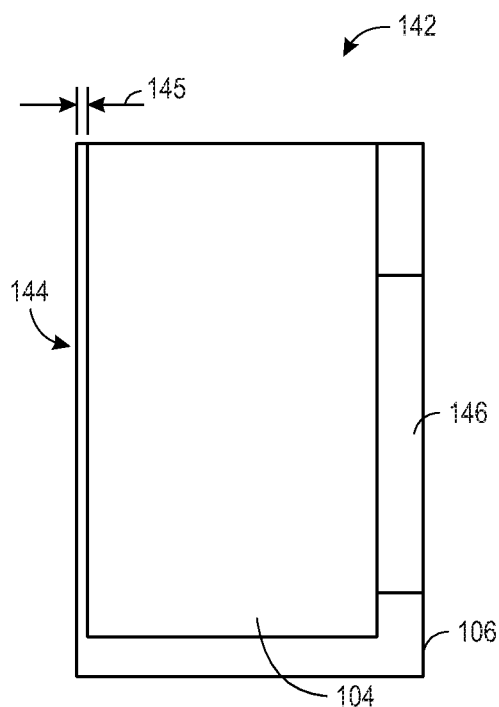
FIG. 10C is a schematic diagram of a cuvette with a single conductive terminal, which may include a capacitive element, in accordance with an embodiment of the present approach.

In some embodiments, the capacitive element 36 may be a structure disposed in the cuvette 20 or a structure that is a part of the cuvette 20 itself. For illustrative purposes, FIG. 9 provides an illustration of a traditional cuvette 152 without a capacitive element. The traditional cuvette 152 may have a cavity 104 used for sample placement (e.g., a sample cavity). Cavity 104 may be formed by a body 106 of the cuvette. The body 106 of the cuvette may be constructed using a nonconductive material (e.g., quartz, plastic). The body of the cuvette may have two opposite walls, wall 124A and 124B. When disposed in a sample holder 26, the walls 124A and 124B may be adjacent to electrodes 16 and 18 of the sample holder 26, respectively. To form an electrical circuit with the pulse generating system 10, the sample wall 124A may have an electrode 156A wall 124B may have a second electrode 156B. In some embodiments, the sample holder 26 may have a spring-loaded mechanism that pushes electrodes 16 and 18 of the sample holder 26 against electrodes 156A and 156B of the cuvette 152. In the traditional cuvette 152, electrodes 156A and 156B provide a conductive (e.g., resistive, non-capacitive) path between the cavity 104 and the electrodes 16 and 18 of the sample holder through walls 124A and 124B of the body 106. To that end, electrodes 156A and 156B may, each, have an internal surface exposed to the cavity.

With the foregoing in mind, FIGS. 10A, 10B, 10C, and 11 illustrate non-limiting example of cuvettes that may include the capacitive element 36. For example, the cuvette 102 in FIG. 10A may include a capacitive element by employing conductive electrodes that are separated from the cavity 104 by a dielectric gaps 114A and 114B. Cuvette 102 may have a cavity 104 for placement of the sample. Cuvette 102 may further include a body 106 constructed using a nonconductive material. To form an electric circuity with electrodes 16 and 18, cuvette 102 includes conductive contacts 108A and 108B. In cuvette 102, the conductive contacts 108A and 108B are separated from the cavity 104 by dielectric gaps 114A and 114B, which form the capacitive element of cuvette 102. The dielectric gaps 114A and 114B may provide a capacitive coupling between a sample in cavity 104 and electrodes 16 and 18 of the sample holder. The capacitance of the capacitive coupling is determined by the dielectric material along the dielectric gaps 114A and 114B, which may be the same as the material used in the body 106 (e.g., plastic, quartz). The capacitance of the capacitive coupling is also determined by the length of the dielectric gaps 114A and 114B and the height of the conductive contacts 108A and 108B. In fact, the distances of the dielectric gaps 114A and 114B may be adjusted to tune the capacitance, and may be chosen based on the suitability of the capacitance for a specific application, for example, platelet activation. The dielectric gaps 114A and 114B may, for example, be in a range between about 0.1 mm and about 5 mm.

The capacitance may be provided without the use of conductive contacts. Cuvette 122 in FIG. 10B without conductive contacts is illustrated. In cuvette 122, the walls 124A and 124B of the capacitor may form the dielectrics for the capacitive element 36 when connected to the electrodes 16 and 18 of the pulse generating system 10. In such system, the thickness 126A and 126B of walls 124A and 124B, respectively, may be determine the capacitance of the capacitive coupling, as discussed above with respect to capacitor 102. Moreover, the dielectric properties of the material used in the construction of the body 106 may further determine the capacitance. In fact, the thickness 126A and the thickness 126B may be adjusted to achieve a capacitance value that is suitable for specific applications such as, for example, platelet activation. Thicknesses 126A and/or 126B may, for example, in a range between about 1 mm and about 5 mm.

Cuvettes 102 and 122, each, employ two separate dielectric regions (e.g., dielectric gaps 114A and 114B, thicknesses 126A and 126B) to form the capacitive coupling. Thus, in such systems, the nominal capacitance may depend on the accuracy of the manufacturing process. The cuvette 142, in FIG. 10C, may have its capacitive coupling formed by a single dielectric region. Cuvette 142 may have a capacitive element formed by the thickness 145 along the single wall 144. Thickness 145 may, for example, in a range between about 1 mm and about 5 mm. On the opposite wall, the cuvette 142 may have an electrode 146 that couples the interior of cavity 104 to the exterior of the cuvette using a conductive (e.g., resistive, non-capacitive) path. As such, when placed in the sample holder, cuvette 142 may form a capacitive coupling between a sample in cavity 104 along the wall 145, and a resistive coupling between a sample in cavity 104 through electrode 146. Note that, as discussed above, the capacitance in the capacitive coupling in cuvette 142 may be determined by the dielectric properties of the material used to form the body 106, as well as the thickness 145 of wall 144.

Figure 11:
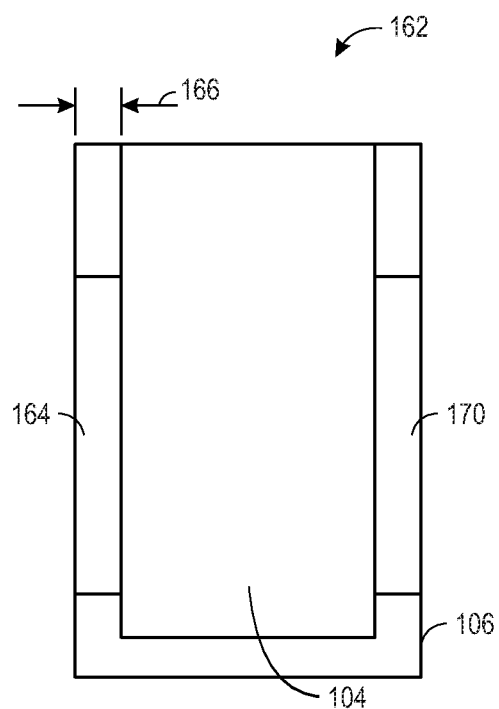
FIG. 11 is a schematic diagram of a cuvette with an additional dielectric element which may form the capacitive element, in accordance with an embodiment of the present approach.

In some embodiments, the dielectric material that provides the capacitive coupling may be a material that is different from the nonconductive material used to form the body 106. Cuvette 162 in FIG. 11 illustrates a capacitive coupling that may be formed by a dielectric 164 that provides the capacitance. The thickness 166 of the dielectric 164 may determine the capacitance of the dielectric. Thickness 145 may, for example, in a range between about 1 mm and about 5 mm. The dielectric 164 may, for example, be a ceramic dielectric, a plastic dielectric, a crystal dielectric, or any other non-conductive material. Cuvette 162 may also include an electrode 170 that couples the interior of cavity 104 to the exterior of the cuvette through a conductive (e.g., resistive, non-capacitive) path. Note further that, in some embodiments, a sample collection device may be used as the capacitive element. For example, if the system 10 is used for platelet activation, a sample collection device, for example, the syringe used to collect the sample 24 (i.e., blood), may have electrodes, dielectric structures, or walls with well-defined thickness, which may be used as both a sample holder and a capacitive element. The overall capacitance provided by embodiments such as the cuvettes of FIGS. 10A, 10B, 10C, and 11, may be in a range between 1 nF and 1 mF.

In some embodiments, the pulse generation system 10 using capacitive coupling may be configured to generate bipolar pulses. The processor 28 may control the pulse generating circuitry 12 such that two electric pulses, one after the other, may be generated. These two electric pulses may have the same pulse duration. However, the amplitude of the electric pulses may be additive inverses. For example, the first electric pulse may have an electric field strength of 50 kV/cm, while the second electric pulse may have an electric field strength of −50 kV/cm. As will be appreciated, the first pulse may have a positive polarity and the second pulse a negative polarity or vice versa, so long as the polarity of the first pulse is opposite that of the second pulse.

Pulse generation systems using capacitive coupling may have benefits related to the results of electrically stimulating the samples. For example, in platelet activation techniques using electrical stimulation, the rate of growth factor release may vary based on the types of electric pulses emitted by a capacitively coupled pulse generation system. For instance, an electric pulse a may cause a growth factor I to be immediately released, and a growth factor J to be subsequently released. On the other hand, an electric pulse b may cause a steady rate of release for growth factor I, while halfway through the process growth factor J is released. The characteristics for the pulses associated with varying growth factor release may be determined by empirical studies. These pulse configurations may be incorporated into the protocols stored on the memory 30, or may be specified by user input.

Figure 4:
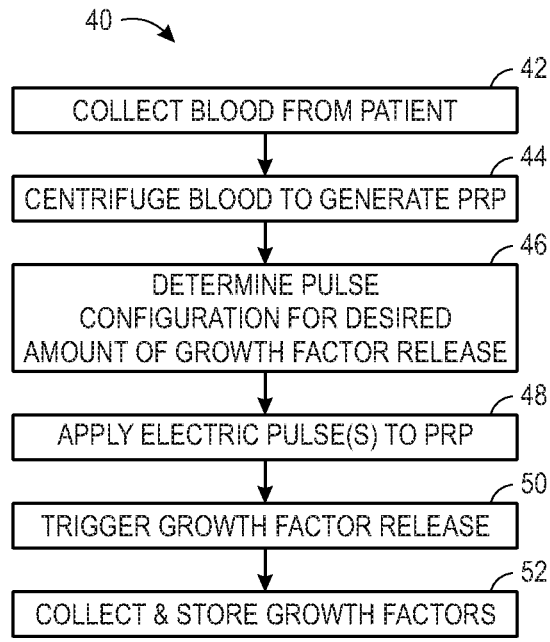
FIG. 4 is a flow chart illustrating a method for ex vivo growth factor release, in accordance with an embodiment of the present approach.

A method 40 for triggering growth factor release, as illustrated in FIG. 4, may be used in conjunction with the system 10. It should be understood that certain steps of the method 40 may be performed by an operator while other steps of the method may be performed by the system 10. At step 42, personnel (e.g., a doctor or nurse) draw blood from a patient, which is centrifuged to generate a platelet rich plasma (PRP) sample in step 44. In the depicted implementation, personnel determine the pulse sequence and configuration of one or more pulses to apply to the PRP sample in the cuvette to trigger a specific or desired amount of released growth factors in step 46. In some systems, the capacitance may be changed. This may take place, for example, in an embodiment having a switch or a removable capacitor. Change in capacitance may also be achieved by changing cuvettes that carry the capacitive element. In such system, step 46 may include an optional process in which the user may enter the configured capacitance. For example, a user may enter the state of the switch, the capacitance of the capacitor, or the capacitance associated with the cuvette. In some systems, the cuvette or the removable capacitor may have a tag (e.g., a label, a code, a bar code, a QR code, or a combination thereof) which may be provided to the pulse generating system. The tag may be associated with characteristics of the cuvette, such as the type of cuvette, capacitance associated with the cuvette, a material of the cuvette, or the prescribed use of the cuvette. The processor may adjust the configuration of the pulses based on the capacitance arranged in the system. In other embodiments, personnel may determine the correct sequence of pulses based on the desired type of released growth factors and/or desired rate of the release of growth factors. During step 48, the PRP sample is exposed to the one or more pulses, which triggers growth factor release in step 50. Finally, in step 52, the growth factors are collected from the PRP sample.

While certain applications may benefit from capacitive coupling, others may benefit from direct coupling. As such, it may be desirable for the pulse generation system 10 to be able to couple capacitively or directly to the load 14 based on the intended biological application (e.g., platelet activation). For example, as mentioned above, the capacitive element 36 may be a capacitor disposed between the electrode 16 and the sample holder 26. The capacitor 36 may be removable, such that the system 10 normally uses direct coupling, and when capacitive coupling is desired, the capacitor 36 is attached, in some embodiments, by an operator. Similarly, an operator may use a conductive sample holder 26 when direct coupling is desired and a nonconductive sample holder 26 when capacitive coupling is desired.

Figure 5:
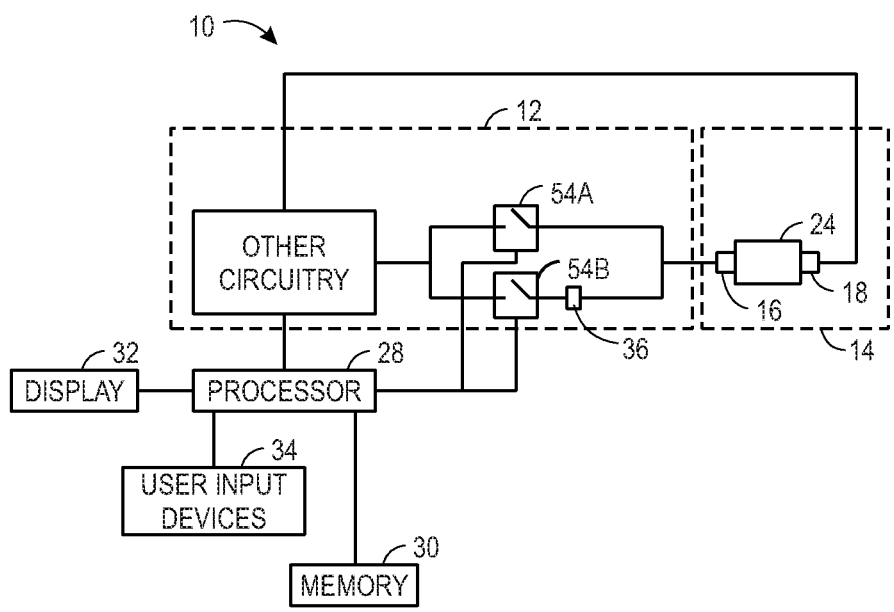
FIG. 5 is a schematic of a pulse generation system both capacitively and directly coupled to a load, in accordance with an embodiment of the present approach.

Alternatively, the pulse generating circuitry 12 may include circuitry that allows current to flow directly to the load 14 (i.e., direct coupling) or routes current through a capacitive element 36 (i.e., capacitive coupling) prior to the load 14, as illustrated in FIG. 5. For example, the pulse generating circuitry 12 may include, in parallel, a direct coupling to the load 14 and the capacitive element 36 (e.g., a capacitor) in series with the load 14 (i.e., capacitive coupling). The processor 28 may control two switches 54A and 54B that allow current to flow to the load 14 via either direct coupling or capacitive coupling approach. The switches 54A and 54B may be any device capable of being selectively changed between an electrically conductive state and a nonconductive state, such as silicon-controlled rectifiers, power transistors, relay switches, or any other like devices. Alternatively, the processor 28 may control other devices, such as analog or digital multiplexors, that are capable of selecting the circuitry associated with the desired coupling approach or scheme. The processor 28 may receive a user input specifying which coupling scheme the system 10 should use. The protocols stored on the memory 30 specifying the characteristics of the pulses generated may also specify whether to use direct or capacitive coupling. Some applications may also benefit from a series of electric pulses delivered to the load 14 that alternate between direct and capacitive coupling. This may take place by having an active controller adjusting switches 54A and 54B, for example. Such configurations may be incorporated into the protocols stored on the memory 30, or may be specified by user input.

EXAMPLES

Controlling the Amount of Growth Factor Release During Platelet Activation

Figure 6:
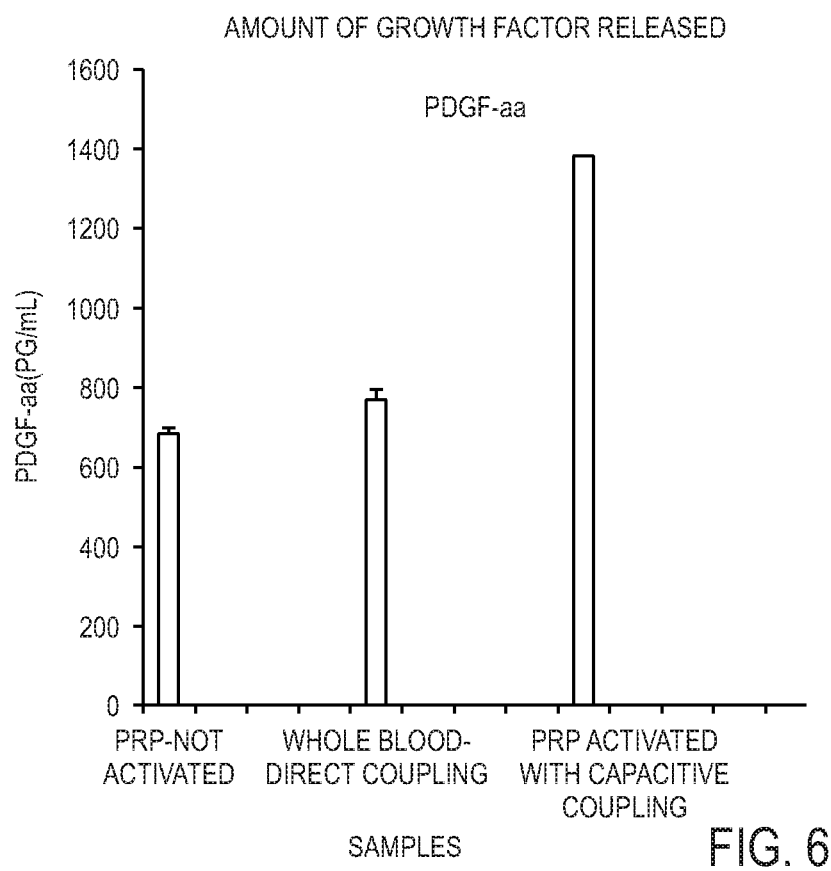
FIG. 6 is a graph displaying the amount of platelet derived growth factor released in unactivated PRP, an unactivated whole blood sample, and a PRP sample capacitively coupled to the pulse generation system.

FIG. 6 depicts the amount of growth factor release in various types of blood samples exposed to electrical stimulation, along with a capacitive coupling approach. Results are shown for samples that include a platelet rich plasma (PRP) sample that has not been activated, a whole blood sample that has not been activated, and a PRP sample that has been activated via electrical stimulation in a capacitively coupled pulse generation system. The PRP samples were exposed to bipolar pulses with a voltage of 700 V (electric field strength of 3.5 kV/cm) and a current of 30 A for a predetermined duration (which may be between 1 ns and 1 s. As illustrated, the amount of platelet-derived growth factor (PDGF) present in the capacitively coupled PRP sample is about twice that of the non-activated PRP sample and the whole blood sample.

Figure 7:
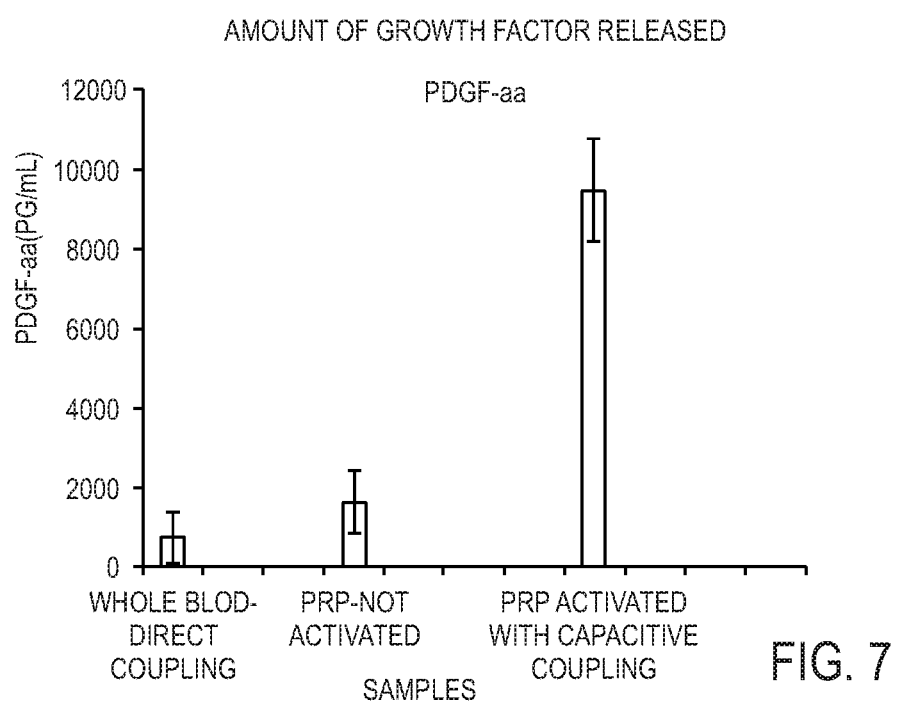
FIG. 7 is a graph displaying the amount of platelet derived growth factor released in unactivated PRP, an unactivated whole blood sample, and a PRP sample capacitively coupled to the pulse generation system.
Figure 8:
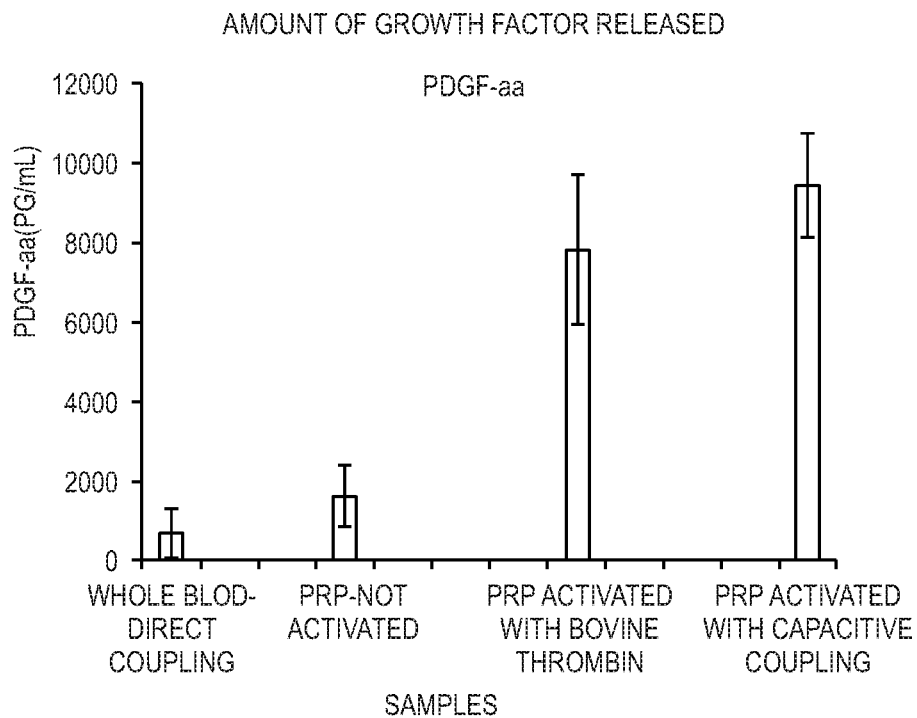
FIG. 8 is a graph displaying the amount of platelet-derived growth factor released in various blood samples using various approaches, including approaches discussed herein.

FIG. 7 illustrates the amount of growth factor release in similar types of samples as in FIG. 6—but a higher capacitive coupling voltage triggers more growth factor release compared to the baseline, non-activated PRP and whole blood. Here, the PRP sample subjected to capacitive coupling was exposed to bipolar pulses with a voltage of 1200 V (electric field strength of 6 kV/cm) and a current of 60 A. The amount of PDGF released in the capacitively coupled PRP sample was six times more than that of the non-activated PRP sample and about thirteen times more than that of the whole blood sample. As shown, the voltage and current characteristics of the electrical stimulation affect the amount of growth factor released compared to the baseline when the pulse generation system is capacitively coupled to the sample. To further illustrate the effectiveness of the capacitively coupled pulse generation system, FIG. 8 compares the amount of PDGF released in a non-activated PRP sample, a whole blood sample not exposed to electrical stimulation, a blood sample activated with bovine thrombin, and a capacitively coupled PRP sample. Note that, as illustrated in FIG. 8, the capacitive coupling may increase the amount of PRP sample that is activated.

One or more of the disclosed embodiments, alone or in combination, may provide one or more technical effects useful for providing pulsed power in various applications. Certain embodiments may allow operators to use nonconductive materials for sample holders in pulse generation systems. For example, the present capacitively coupled pulse generation system may use a syringe or other plastic container, instead of a cuvette, as a sample holder. These nonconductive samples holders may be less expensive, easier to sterilize, and more readily available than sample holders used in conventional pulse generation systems. Additionally, samples that are electrically stimulated using the present capacitively coupled pulse generation system may differ based on the types of pulses used. For instance, varying the pulse parameters for the present capacitively coupled pulse generation system for treating the sample, for example, in the platelet activation application, may modify the amount of growth factors released from the sample. Other embodiments may also allow operators to use direct or capacitive coupling in pulse generation systems. For example, the present pulse generation system may contain suitable control and pulse generating circuitry that allows current to flow directly to the sample (i.e., direct coupling) or reroutes the current through a capacitive element (i.e., capacitive coupling). The technical effects and technical problems in the specification are exemplary and not limiting. It should be noted that the embodiments described in the specification may have other technical effects and can solve other technical problems.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A cuvette comprising:
a body comprising a nonconductive material;
a sample cavity configured to receive a sample;
a first wall configured to couple to a first electrode of a pulse generating system that comprises a capacitive element, wherein the capacitive element is in series with the sample during operation; and
a second wall configured to couple to a second electrode of the pulse generating system.

2. The cuvette of claim 1, wherein the capacitive element comprises a capacitance in a range between 1 nF and 1 mF.

3. The cuvette of claim 1, wherein the nonconductive material comprises a quartz or a plastic.

4. The cuvette of claim 1, wherein the first wall comprises a conductive contact configured to couple to the first electrode to the capacitive element, wherein the conductive contact is separated from the sample cavity by a dielectric gap of the capacitive element, and wherein the dielectric gap comprises the nonconductive material.

5. The cuvette of claim 4, wherein the dielectric gap comprises a first thickness between about 1 mm and 5 mm.

6. The cuvette of claim 1, wherein the second wall comprises a second capacitive element.

7. The cuvette of claim 1, wherein the first wall comprises a dielectric element.

8. The cuvette of claim 7, wherein the dielectric element comprises a ceramic dielectric or a plastic dielectric.

9. The cuvette of claim 1, wherein the second wall comprises a conductive contact configured to couple the second electrode directly to the sample cavity.

10. The cuvette of claim 1, comprising a label that comprises a tag associated with a capacitance of the capacitive element of the cuvette.

11. The cuvette of claim 1, wherein the first wall is configured to receive a current from the pulse generating system, wherein the current flows through the capacitive element prior to the current reaching the first electrode.

12. The cuvette of claim 1, wherein the first wall is configured to receive a current from the pulse generating system, wherein pulse generating system comprises the capacitive element configured to receive the current prior to the current reaching the first electrode.

* * * * *